United States Patent
Birkbeck et al.

(10) Patent No.: US 11,225,629 B2
(45) Date of Patent: Jan. 18, 2022

(54) VETIVER ODORANT

(71) Applicant: FIRMENICH SA, Geneva (CH)

(72) Inventors: Anthony Alexander Birkbeck, Geneva (CH); Pascal Millet, Geneva (CH)

(73) Assignee: FIRMENICH SA, Geneva (CH)

( * ) Notice: Subject to any disclaimer, the term of this patent is extended or adjusted under 35 U.S.C. 154(b) by 60 days.

(21) Appl. No.: 16/500,624

(22) PCT Filed: Mar. 29, 2018

(86) PCT No.: PCT/EP2018/058201
§ 371 (c)(1),
(2) Date: Oct. 3, 2019

(87) PCT Pub. No.: WO2018/185010
PCT Pub. Date: Oct. 11, 2018

(65) Prior Publication Data
US 2021/0108153 A1    Apr. 15, 2021

(30) Foreign Application Priority Data
Apr. 4, 2017   (EP) .................................... 17164794

(51) Int. Cl.
*C11B 9/00*    (2006.01)
*C07C 49/553*  (2006.01)
*C11D 3/50*    (2006.01)

(52) U.S. Cl.
CPC .......... *C11B 9/0053* (2013.01); *C07C 49/553* (2013.01); *C11D 3/50* (2013.01); *C07C 2602/28* (2017.05)

(58) Field of Classification Search
CPC .......................... C07C 49/553; C11B 9/0053
See application file for complete search history.

(56) References Cited

U.S. PATENT DOCUMENTS

| | | |
|---|---|---|
| 3,911,018 A | 10/1975 | Hall et al. |
| 4,107,208 A | 8/1978 | Schreiber et al. |
| 4,396,670 A | 8/1983 | Sinclair |

FOREIGN PATENT DOCUMENTS

| | | |
|---|---|---|
| EP | 2005939 A1 | 12/2008 |
| WO | 0141915 A1 | 6/2001 |

OTHER PUBLICATIONS

Belhassen et al.,"Volatile constuents of vetiver: a review", Flavour and Fragrance Journal., Dec. 22, 2014, pp. 26-82, vol. 30-1.
International Search Report and Written Opinion for Internation Application No. PCT/EP2018/058201, dated Jun. 20, 2018. 13 pages.
Dietrich et al., Acta Polymerica, 1989, pp. 683-690, vol. 40-11.
Dietrich et al., Acta Polymerica, 1989, pp. 243-251, vol. 40-4.
Dietrich et al., Acta Polymerica, 1990, pp. 91-95, vol. 41-2.
Lee et al, "Microencapsulation of fragrant oil via in situ polymerization: effects of pH and melamine-fomaldehyde molar ratio", Journal of Microencapsulation, 2002, pp. 559-569 vol. 19-5.
Bone et al.,"Microencapsulated Fragrances in Melamine Formaldehyde Resins", Chimia, 2011, pp. 177-181, vol. 65-3.
Kulkarini et al,"Synthesis of a ketodicarboxylic acid related to elemol and epidihydroeudesmol", Tetrahedron, 1965, pp. 1167-1173, vol. 21.
Maurer et al, "Zur Kennnis der sesquiterpenoiden C12-Ketone des ätherischen Öls von *Vetiveria zizanioides* (L.) Nash", Helvetica Chimica Acta, 1972,p. 2371-2382, 55.—English Abstract Only.

*Primary Examiner* — Arrie L Reuther
(74) *Attorney, Agent, or Firm* — Armstrong Teasdale LLP

(57) ABSTRACT

Compounds of formula (I) in the form of any one of its stereoisomers or a mixture thereof are provided, wherein the dotted lines represent a carbon-carbon single bond or a carbon-carbon double bond; and one $R^1$ group represents a hydrogen atom and the second $R^1$ group represents a methyl group. Also provided are their uses as perfuming ingredients to impart vetiver/rooty and powdery notes; e.g. in perfuming compositions or in consumer products.

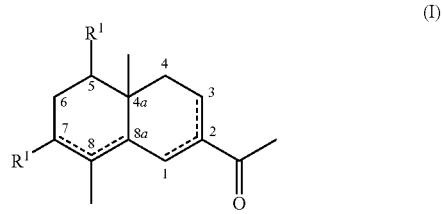

14 Claims, No Drawings

VETIVER ODORANT

CROSS-REFERENCE TO RELATED APPLICATIONS

This application is a U.S. National Phase Application of PCT/EP2018/058201, filed on Mar. 29, 2018, which claims the benefit of priority to European Patent Application Number 17164794.4, filed Apr. 4, 2017, the entire contents of which are hereby incorporated by reference herein.

TECHNICAL FIELD

The present invention relates to the field of perfumery. More particularly, it concerns the compound of formula (I) as defined herein below, and their uses as perfuming ingredients, e.g. in perfuming compositions and/or consumer products.

PRIOR ART

The perfumery industry is constantly on the lookout for new ingredients in order to support the creativity of perfumer by diversifying the notes present in their palette. One of the key organoleptic families in perfumery is the woody note which is very important in perfumery creation.

The present invention provides a new compound belonging to this family. Actually, the compound of formula (I) as reported in the present invention imparts a very interesting woody note.

To the best of our knowledge the compound of formula (I) is novel and the only related analogue reported in the literature, and described for its odor properties, is 1-[(4aRS, 8SR,8aSR)-4a,8-dimethyl-3,4,4a,5,6,7,8,8a-octahydro-2-naphthalenyl]ethanone, i.e. a derivative having a syn configuration between the two methyl groups at carbon 4a and 8 (see N. Baldovini et al, in *Flavour Frag. J.*, 2015, 30, 26). Said prior art analogue has been defined in nature and described has having a woody-fruity damascone odor, i.e. significantly different from the any one of the present compounds.

The prior art document does not report or suggest any organoleptic properties of the compound of formula (I), or any use of said compound in the field of perfumery.

SUMMARY OF THE INVENTION

The invention relates to compound of formula (I) which imparts an odor of woody/rooty and powdery type which is very appreciated in perfumery.

So, a first object of the present invention is a use of a compound of formula

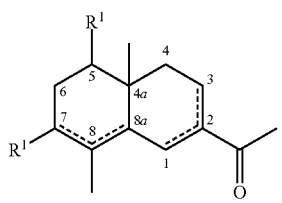
(I)

in the form of any one of its stereoisomers or a mixture thereof, wherein the dotted lines represent a carbon-carbon single bond or a carbon-carbon a double bond; and one $R^1$ group represents a hydrogen atom and the second $R^1$ group represents a methyl group.

A second object of the invention is a compound of formula (I) as defined above.

A third object of the invention is a perfuming composition comprising
i) at least one compound of formula (I), as defined above;
ii) at least one ingredient selected from the group consisting of a perfumery carrier and a perfumery base; and
iii) optionally at least one perfumery adjuvant.

Another object of the invention is a perfumed consumer product comprising at least one compound of formula (I) as defined above or a perfuming composition as defined above.

A last object of the invention is a method to confer, enhance, improve or modify the odor properties of a perfuming composition or of a perfumed article, which method comprises adding to said composition or article an effective amount of at least a compound of formula (I) as defined above.

DESCRIPTION OF THE INVENTION

We have now surprisingly discovered a compound of formula (I) imparting a very powerful woody type note.

So the first object of the present invention is a use of a compound of formula

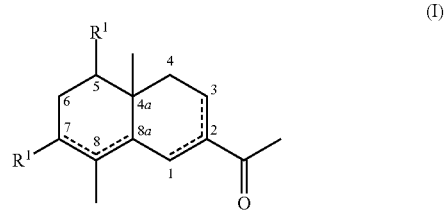
(I)

in the form of any one of its stereoisomers or a mixture thereof, wherein the dotted lines represent a carbon-carbon single bond or a carbon-carbon double bond; and one $R^1$ group represents a hydrogen atom and the second $R^1$ group represents a methyl group.

Said compounds can be used as perfuming ingredient, for instance to impart a powerful odor notes of the woody type in the direction of vetiver/rooty type and surprisingly also of the powdery type.

For the sake of clarity, by the expression "any one of its stereoisomers or a mixture thereof", or the similar, it is meant the normal meaning understood by a person skilled in the art, i.e. that the invention's compound can be a pure enantiomer or diastereomer (e.g. the hydrogen atom on the carbon 8a in a syn or anti conformation relative to the methyl group in position 4a and carbon 5 or 7 bearing a methyl group in a syn conformation relative to the methyl group in position 4a). In other words, the invention's compound possesses up to 5 stereocenters, preferably 4 stereocenters, i.e. carbon 2, 4a, 8, 8a and 5 or 7, preferably carbon 4a, 8, 8a and 5 or 7. Each of said stereocenter can have two different stereochemistries (e.g. R or S). The compound may even be in the form of a pure enantiomer or in the form of a mixture of enantiomers or diastereoisomers. The invention's compound can be in a racemic form or scalemic form. Therefore the compound of formula (I) can be one stereoisomers or in the form of a composition of matter comprising, or consisting of, various stereoisomers. Preferably, the two methyl groups at carbon 4a and 8 are in an anti-configuration either relative or absolute.

For the sake of clarity, by the expression "the dotted lines represent a carbon-carbon single bond or a carbon-carbon double bond", or the similar, it is meant the normal meaning understood by a person skilled in the art, i.e. that the whole bonding (solid and dotted line) between the carbon atoms connected by said dotted line, e.g. carbon 1 and 2, is a carbon-carbon single or double bond; provided that two adjoining dotted lines are not both double bonds; i.e. when the bond between carbon 1 and carbon 2 is a double bond, the bond between carbon 2 and carbon 3 will be a single bond.

According to any one of the above embodiments of the invention, at most two non-adjoining dotted lines represent a carbon-carbon double bond and the others a carbon-carbon single bond According to any one of the above embodiments of the invention, compound (I) can be a compound of formula

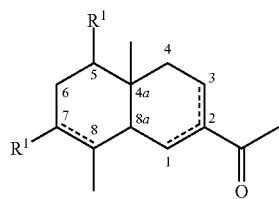

(II)

in the form of any one of its stereoisomers or a mixture thereof, and wherein at least one dotted line represents a carbon-carbon single bond and the others a carbon-carbon double bond; and one $R^1$ group represents a hydrogen atom and the second $R^1$ group represents a methyl group. Preferably, two dotted lines represent a carbon-carbon single bond and the other a carbon-carbon double bond.

According to a particular embodiment of the invention, compound (I) can be a compound of formula

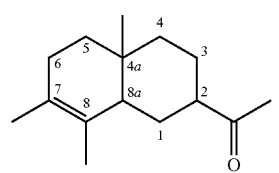

(III)

in the form of any one of its stereoisomers or a mixture thereof.

According to any one of the above embodiments of the invention, compound (I) can be a compound of formula

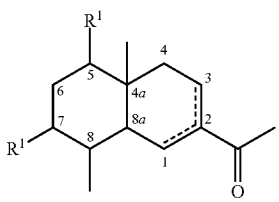

(IV)

in the form of any one of its stereoisomers or a mixture thereof, and wherein one dotted line represents a carbon-carbon single bond and the other a carbon-carbon double bond; and one $R^1$ group represents a hydrogen atom and the second $R^1$ group represents a methyl group.

According to any one of the above embodiments of the invention, compound (I) can be a compound of formula

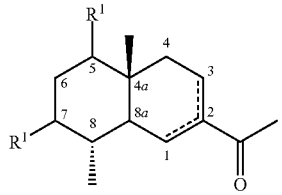

(V)

in the form of any one of its stereoisomers or a mixture thereof, and wherein the bold and hatched lines indicate a relative or absolute configuration; one dotted line represents a carbon-carbon single bond and the other a carbon-carbon double bond; and one $R^1$ group represents a hydrogen atom and the second $R^1$ group represents a methyl group.

For the sake of clarity, by the expression "the bold and hatched lines indicate a relative or absolute configuration" or the similar, it is meant the normal meaning understood by a person skilled in the art, i.e. that in the case of an relative configuration compound (I) is in the form of a mixture of stereoisomers comprising more than 50% (w/w) of the (4aRS,8RS) stereoisomer when carbon 7 bears $R^1$ being a methyl group, i.e. a compound having the two methyl groups in a relative trans configuration as shown in formula (I), or in the case of an absolute configuration compound (I) is in the form of a mixture of stereoisomers comprising more than 50% (w/w) of the (4aS,8S) stereoisomer when carbon 7 bears $R^1$ being a methyl group.

For the sake of clarity, by the expression "(4aRS,8RS)" it is meant an equimolar mixture of (4aR,8R) and (4aS,8S).

According to a particular embodiment of the invention, said compound (VI) is a compound of formula

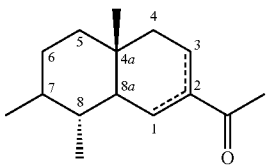 [SMILES: CC(=O)C1=CC[C@@]2(C)CCC(C)[C@@H](C)C2C1]

(VI)

in the form of any one of its stereoisomers or a mixture thereof, and wherein the bold and hatched lines indicate a relative or absolute configuration; and one dotted line represents a carbon-carbon single bond and the other a carbon-carbon double bond.

According to a particular embodiment of the invention, compound (VI) may be 1-((4aRS,8RS)-4a,7,8-trimethyl-1,4,4a,5,6,7,8,8a-octahydronaphthalen-2-yl)ethan-1-one, 1-((4aRS,8RS)-4a,7,8-trimethyl-3,4,4a,5,6,7,8,8a-octahydronaphthalen-2-yl)ethan-1-one or a mixture thereof. More particularly, compound (VI) may be 1-((4aRS,7SR,8RS, 8aRS)-4a,7,8-trimethyl-1,4,4a,5,6,7,8,8a-octahydronaphthalen-2-yl)ethan-1-one, 1-((4aRS,7RS,8RS,8aRS)-4a,7,8-trimethyl-1,4,4a,5,6,7,8,8a-octahydronaphthalen-2-yl)

ethan-1-one, 1-((4aRS,7RS,8RS,8aSR)-4a,7,8-trimethyl-1,4,4a,5,6,7,8,8a-octahydronaphthalen-2-yl)ethan-1-one, 1-((4aRS,7SR,8RS,8aSR)-4a,7,8-trimethyl-1,4,4a,5,6,7,8,8a-octahydronaphthalen-2-yl)ethan-1-one, 1-((4aRS,7SR,8RS,8aSR)-4a,7,8-trimethyl-3,4,4a,5,6,7,8,8a-octahydronaphthalen-2-yl)ethan-1-one, 1-((4aRS,7RS,8RS,8aSR)-4a,7,8-trimethyl-3,4,4a,5,6,7,8,8a-octahydronaphthalen-2-yl)ethan-1-one, 1-((4aRS,7RS,8RS,8aRS)-4a,7,8-trimethyl-3,4,4a,5,6,7,8,8a-octahydronaphthalen-2-yl)ethan-1-one, 1-((4aRS,7SR,8RS,8aRS)-4a,7,8-trimethyl-3,4,4a,5,6,7,8,8a-octahydronaphthalen-2-yl)ethan-1-one or a mixture thereof.

According to any embodiment of the invention, said compound (V) is a compound of formula

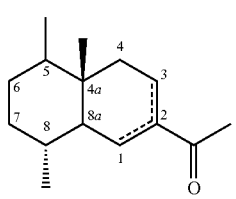

(VII)

in the form of any one of its stereoisomers or a mixture thereof, and wherein the bold and hatched lines indicate a relative or absolute configuration; and one dotted line represents a carbon-carbon single bond and the other a carbon-carbon double bond.

According to a particular embodiment of the invention, compound (VII) may be 1-((4aSR,8RS)-4a,5,8-trimethyl-1,4,4a,5,6,7,8,8a-octahydronaphthalen-2-yl)ethan-1-one, 1-((4aSR,8RS)-4a,5,8-trimethyl-3,4,4a,5,6,7,8,8a-octahydronaphthalen-2-yl)ethan-1-one or a mixture thereof. More particularly compound (VII) may be 1-((4aSR,5RS,8RS,8aRS)-4a,5,8-trimethyl-1,4,4a,5,6,7,8,8a-octahydronaphthalen-2-yl)ethan-1-one, 1-((4aSR,5SR,8RS,8aRS)-4a,5,8-trimethyl-1,4,4a,5,6,7,8,8a-octahydronaphthalen-2-yl)ethan-1-one, 1-((4aSR,5SR,8RS,8aSR)-4a,5,8-trimethyl-1,4,4a,5,6,7,8,8a-octahydronaphthalen-2-yl)ethan-1-one, 1-((4aSR,5RS,8RS,8aSR)-4a,5,8-trimethyl-1,4,4a,5,6,7,8,8a-octahydronaphthalen-2-yl)ethan-1-one, 1-((4aSR,5RS,8RS,8aSR)-4a,5,8-trimethyl-3,4,4a,5,6,7,8,8a-octahydronaphthalen-2-yl)ethan-1-one, 1-((4aSR,5SR,8RS,8aSR)-4a,5,8-trimethyl-3,4,4a,5,6,7,8,8a-octahydronaphthalen-2-yl)ethan-1-one, 1-((4aSR,5SR,8RS,8aRS)-4a,5,8-trimethyl-3,4,4a,5,6,7,8,8a-octahydronaphthalen-2-yl)ethan-1-one, 1-((4aSR,5RS,8RS,8aRS)-4a,5,8-trimethyl-3,4,4a,5,6,7,8,8a-octahydronaphthalen-2-yl)ethan-1-one or a mixture thereof.

In the present invention the term "compound of formula (I)" is constructed in order to encompass also all composition of matter resulting from the admixture of at least two chemicals responding to formula (I). In particular, said compound of formula (I) can be in the form of a composition of matter comprising compound (III), compound (VI) and compound (VII). As non-limiting example, compound of formula (I) can be in the form of a composition of matter comprising, or consisting of:

1-((4aRS,8aRS)-4a,7,8-trimethyl-1,2,3,4,4a,5,6,8a-octahydronaphthalen-2-yl)ethan-1-one;
1-((4aSR,8SR)-4a,7,8-trimethyl-1,4,4a,5,6,7,8,8a-octahydronaphthalen-2-yl)ethan-1-one;
1-((4aSR,8SR)-4a,7,8-trimethyl-3,4,4a,5,6,7,8,8a-octahydronaphthalen-2-yl)ethan-1-one;
1-((4aRS,8SR)-4a,5,8-trimethyl-1,4,4a,5,6,7,8,8a-octahydronaphthalen-2-yl)ethan-1-one; and
1-((4aRS,8SR)-4a,5,8-trimethyl-3,4,4a,5,6,7,8,8a-octahydronaphthalen-2-yl)ethan-1-one.

As specific examples of the invention's compounds, one may cite, as non-limiting example, a mixture of 1-((4aRS,8aRS)-4a,7,8-trimethyl-1,2,3,4,4a,5,6,8a-octahydronaphthalen-2-yl)ethan-1-one, 1-((4aRS,8RS)-4a,7,8-trimethyl-1,4,4a,5,6,7,8,8a-octahydronaphthalen-2-yl)ethan-1-one, 1-((4aRS,8RS)-4a,7,8-trimethyl-3,4,4a,5,6,7,8,8a-octahydronaphthalen-2-yl)ethan-1-one, 1-((4aSR,8RS)-4a,5,8-trimethyl-1,4,4a,5,6,7,8,8a-octahydronaphthalen-2-yl)ethan-1-one and 1-((4aSR,8RS)-4a,5,8-trimethyl-3,4,4a,5,6,7,8,8a-octahydronaphthalen-2-yl)ethan-1-one which has a very good woody odor in the direction of vetiver/rooty type in addition to a smoky odor and accompanied to an amber, powdery and violet character. The powdery/iris character of this ingredient is reminiscent of Myrrhone® (4-(2,2,C-3,T-6-tetramethyl-R-1-cyclohexyl)-3-buten-2-one, trademark and origin: Firmenich SA). This mixture is also very powerful.

As non-limiting, examples of the invention's compounds, one may cite the following ones in Table 1:

TABLE 1

Invention's compounds structures and their odor properties

| Compound structure and name | Odor notes |
|---|---|
| | See above: vetiver/rooty, smoky, and powdery odor very powerful |
| | |
| | |
| | |
| as defined in Example 1 | |

TABLE 1-continued

Invention's compounds structures and their odor properties

| Compound structure and name | Odor notes |
|---|---|

Prior art compound

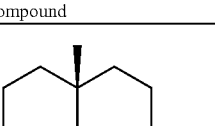

Grapefruit-rhubarb, woody-fruity, damascone like odor

1-[(4aRS,8SR,8aSR)-4a,8-dimethyl-3,4,4a,5,6,7,8,8a-octahydro-2-naphthalenyl]ethanone According to a particular embodiment of the invention, the compound of formula (I) is 1-((4aRS,8aRS)-4a,7,8-trimethyl-1,2,3,4,4a,5,6,8a-octahydronaphthalen-2-yl)ethan-1-one, 1-((4aRS,7SR,8RS,8aRS)-4a,7,8-trimethyl-1,4,4a,5,6,7,8,8a-octahydronaphthalen-2-yl)ethan-1-one, 1-((4aRS,7RS,8RS,8aRS)-4a,7,8-trimethyl-1,4,4a,5,6,7,8,8a-octahydronaphthalen-2-yl)ethan-1-one, 1-((4aRS,7RS,8RS,8aSR)-4a,7,8-trimethyl-1,4,4a,5,6,7,8,8a-octahydronaphthalen-2-yl)ethan-1-one, 1-((4aRS,7SR,8RS,8aSR)-4a,7,8-trimethyl-1,4,4a,5,6,7,8,8a-octahydronaphthalen-2-yl)ethan-1-one, 1-((4aRS,7SR,8RS,8aSR)-4a,7,8-trimethyl-3,4,4a,5,6,7,8,8a-octahydronaphthalen-2-yl)ethan-1-one, 1-((4aRS,7RS,8RS,8aSR)-4a,7,8-trimethyl-3,4,4a,5,6,7,8,8a-octahydronaphthalen-2-yl)ethan-1-one, 1-((4aRS,7RS,8RS,8aRS)-4a,7,8-trimethyl-3,4,4a,5,6,7,8,8a-octahydronaphthalen-2-yl)ethan-1-one, 1-((4aRS,7SR,8RS,8aRS)-4a,7,8-trimethyl-3,4,4a,5,6,7,8,8a-octahydronaphthalen-2-yl)ethan-1-one 1-((4aSR,5RS,8RS,8aRS)-4a,5,8-trimethyl-1,4,4a,5,6,7,8,8a-octahydronaphthalen-2-yl)ethan-1-one, 1-((4aSR,5SR,8RS,8aRS)-4a,5,8-trimethyl-1,4,4a,5,6,7,8,8a-octahydronaphthalen-2-yl)ethan-1-one, 1-((4aSR,5SR,8RS,8aSR)-4a,5,8-trimethyl-1,4,4a,5,6,7,8,8a-octahydronaphthalen-2-yl)ethan-1-one, 1-((4aSR,5RS,8RS,8aSR)-4a,5,8-trimethyl-1,4,4a,5,6,7,8,8a-octahydronaphthalen-2-yl)ethan-1-one, 1-((4aSR,5RS,8RS,8aSR)-4a,5,8-trimethyl-3,4,4a,5,6,7,8,8a-octahydronaphthalen-2-yl)ethan-1-one, 1-((4aSR,5RS,8RS,8aSR)-4a,5,8-trimethyl-3,4,4a,5,6,7,8,8a-octahydronaphthalen-2-yl)ethan-1-one, 1-((4aSR,5SR,8RS,8aRS)-4a,5,8-trimethyl-3,4,4a,5,6,7,8,8a-octahydronaphthalen-2-yl)ethan-1-one, 1-((4aSR,5RS,8RS,8aRS)-4a,5,8-trimethyl-3,4,4a,5,6,7,8,8a-octahydronaphthalen-2-yl)ethan-1-one and/or mixtures thereof.

When the odor of the invention's compounds is compared with that of the prior art compound 1-[(4aRS,8SR,8aSR)-4a,8-dimethyl-3,4,4a,5,6,7,8,8a-octahydro-2-naphthalenyl] ethanone (i.e. the cis compound), then the invention's compounds distinguish themselves by being largely more powerful and by having a powdery/violet/iris character in addition to the woody note.

Furthermore, the woody note associated with the invention's compounds is of the rooty type, i.e. a warm heavy effect, while the woody note associated with the prior art compounds is of the cedar type, i.e. a resin, sawdust, fresh effect. The odor of the invention's compounds distinguish also from the prior art by lacking, or not possessing significant, fruity notes and damsacone notes, which are characteristic of the prior art compound. Said differences, besides being not foreseeable, lend the invention's compounds and the prior art compound to be each suitable for different uses, i.e. to impart different organoleptic impressions.

As mentioned above, the invention concerns the use of a compound of formula (I) as perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac© (origin: Cytec Technology Corp.), Cymel® (origin: Cytec Technology Corp.), Urecoll® or Luracoll® (origin: BASF).

Others resins one are the ones produced by the polycondensation of an polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients knows for having a similar olfactive note, such as: In particular one may cite perfuming co-ingredients which are commonly used in perfume formulations, such as:

Aldehydic ingredients: decanal, dodecanal, 2-methyl-undecanal, 10-undecenal, octanal and/or nonanal;

Aromatic-herbal ingredients: *eucalyptus* oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients:Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4 (2H)-pyranol, beta ionone, methyl 2-(methylamino) benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-methanol, Propyl (S)-2-(1,1-dimethylpropoxy) propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-diméthyléthyl)-1-cyclohexyl acetate, verdyl isobutyrate and/or mixture of methyliononesisomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexanedicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;

Musk ingredients: 1,4-dioxa-5,17-cycloheptadecane-dione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'- dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound (I) is added. Consequently, another object of the present invention consists of by a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 50% by weight, or even more, of the compounds of the invention based on the weight of the composition into which they are incorporated. In the case of perfumed consumer product, typical concentrations are in the order of 0.1% to 20% by weight, or even more, of the compounds of the invention based on the weight of the consumer product into which they are incorporated.

EXAMPLES

The invention will now be described in further detail by way of the following examples, wherein the abbreviations have the usual meaning in the art, the temperatures are indicated in degrees centigrade (° C.); NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C), the chemical shifts δ are indicated in ppm with respect to TMS as standard, the coupling constants J are expressed in Hz.

Example 1

Synthesis of Compounds of Formula (I)—Preparation of a Mixture of 1-((4aRS,8aRS)-4a,7,8-trimethyl-1,2,3,4,4a,5,6,8a-octahydronaphthalen-2-yl)ethan-1-one, 1-(4a,7,8-trimethyl-3,4,4a,5,6,7,8,8a-octahydronaphthalen-2-yl)ethan-1-one, 1-(4a,7,8-trimethyl-1,4,4a,5,6,7,8,8a-octahydronaphthalen-2-yl)ethan-1-one, 1-(4a,5,8-trimethyl-3,4,4a,5,6,7,8,8a-octahydronaphthalen-2-yl)ethan-1-one and 1-(4a,5,8-trimethyl-1,4,4a,5,6,7,8,8a-octahydronaphthalen-2-yl)ethan-1-one a) Preparation of a mixture of 4a,7,8-trimethyl-4,4a,5,6,7,8-hexahydronaphthalen-2(3H)-one and 4a,5,8-trimethyl-4,4a,5,6,7,8-hexahydronaphthalen-2(3H)-one A solution of 2,3,6-trimethylcyclohexanone (108 g, 0.77 mol) and toluenesulfonic acid (2.0 g, 11 mmol) in cyclohexane (200 mL) was warmed to 70° C. and methyl vinyl ketone (54 g, 0.77 mol) was added slowly dropwise. The mixture was heated at 70° C. for a further 15 hours then cooled and treated with 10% NaOH solution. The aqueous phase was re-extracted with diethyl ether, the combined organic phase was washed with brine then dried over $Na_2SO_4$ and filtered and the solvents removed in vacuo to yield as a mixture of cyclized and non-cyclized diketone which was used directly in the next cyclization step 124 g.

2,5,6-trimethyl-2-(3-oxobutyl)cyclohexan-1-one (non-cyclized diketone)

$^1$H (CDCl$_3$, 500 MHz): δ 0.97 (s, 3H), 0.99 (d, J 6.5, 3H), 1.04 (d, J 6.2, 3H), 1.36-1.47 (m, 1H), 1.51-1.75 (m, 4H), 1.82 (dt, J 13.6, 3.3, 1H), 2.03-2.12 (m, 1H), 1.78-1.85 (m, 1H), 1.89 (td, J 14.0, 4.5, 1H), 2.08 (tt, J 13.8, 4.1, 1H), 2.27 (bq, J 7.5, 1H), 2.33-2.38 (m, 1H), 2.56 (ddd, J 17.6, 15, 5.1, 1H), 5.77 (s, 1H) ppm.

13C 99620

$^{13}$C (CDCl$_3$, 125 MHz): δ 12.0 (q), 20.8 (q), 22.4 (q), 30.0 (t)), 30.1 (q), 30.9 (t), 38.2 (t), 39.3 (t), 41.4 (d), 47.0 (s), 47.7 (d), 208.1 (s), 218.4 (s) ppm.

A solution of a mixture of diketone and enones obtained above (mixture of isomers, 104 g, 0.495 mol) and KOH (8.0 g, 142 mmol) in EtOH (35 mL) was heated at 70° C. for 35 hours then cooled. Diluted with ether, the organic phase was washed with sodium bicarbonate then dried over MgSO$_4$ and concentrated in vacuo to yield the crude enone as a complex mixture of isomers, 60 g, 63%. The mixture was purified by Leybold (continuous wiped film) distillation (145° C. vide 0.3 mbar) to give the enone as a mixture of (4aSR,7SR,8RS)-4a,5,8-trimethyl-4,4a,5,6,7,8-hexahydronaphthalen-2(3H)-one, (4aSR,8SR)-4a,7,8-trimethyl-4,4a,5,6,7,8-hexahydronaphthalen-2(3H)-one and (4aSR,8RS)-4a,5,8-trimethyl-4,4a,5,6,7,8-hexahydronaphthalen-2(3H)-one in a respective amount of 8%, 82% and 10%.

Minor isomer: (4aSR,7SR,8RS)-4a,7,8-trimethyl-4,4a,5,6,7,8-hexahydronaphthalen-2(3H)-one $^1$H (CDCl$_3$, 500 MHz): δ 0.94 (d, J 7.4, 3H), 1.25 (d, J 7.4, 3H), 1.31 (s, 3H), 1.31-1.35 (m, 1H), 1.44 (dt, J 13.8, 3.8, 1H), 1.58 (td, J 13.7, 4.1, 1H), 1.69, (ddd, J 13.1, 5.0, 2.4, 1H), 1.78-1.85 (m, 1H), 1.89 (td, J 14.0, 4.5, 1H), 2.08 (tt, J 13.8, 4.1, 1H), 2.27 (bq, J 7.5, 1H), 2.33-2.38 (m, 1H), 2.56 (ddd, J 17.6, 15, 5.1, 1H), 5.77 (s, 1H) ppm.

$^{13}$C (CDCl$_3$, 125 MHz): δ 20.0 (q), 22.9 (q), 23.2 (t), 25.3 (q), 34.3 (t), 34.4 (d), 34.7 (t), 35.5 (s), 40.3 (t), 45.2 (d), 127.2 (d), 174.3 (s), 199.8 (s) ppm.

Major isomer: (4aSR,8SR)-4a,7,8-trimethyl-4,4a,5,6,7,8-hexahydronaphthalen-2(3H)-one $^{13}$C (CDCl$_3$, 125 MHz): δ 12.5, 14.7, 15.9, 21.2, 23.2, 23.4 (q), 29.0, 30.9, 33.6, 33.9 (t), 36.1 (d), 36.1 (t), 36.1, 36.3 (s), 37.7 (d), 38.3, 38.5 (t), 40.3, 40.6 (d), 41.0 (t), 121.9, 123.9 (d), 172.6, 173.8 (s), 198.8, 200.4 (s) ppm.

b) Preparation of a mixture of 4a,7,8-trimethyloctahydronaphthalen-2(1H)-one and 4a,5,8-trimethyloctahydronaphthalen-2(1H)-one Palladized charcoal (5%, Pd/C, 1.42 g) was added to a solution of the enone mixture obtained in step a) (57 g, 296 mmol) in ethyl acetate (80 mL) and the suspension evacuated in vacuo then purged with hydrogen gas (3×) then stirred under an atmosphere of hydrogen gas (2 bar) for 24 hours. The suspension was filtered and washed with ethyl acetate, then the solvents removed in vacuo and the residue further purified by bulb to bulb (Kügelrohr) distillation 150° C. at 0.5 mbar and gave the saturated ketone as a complex mixture of isomers; 60 g, 99%.

Major isomers are:
(4aSR,7RS,8SR,8aRS)-4a,7,8-trimethyloctahydronaphthalen-2(1H)-one $^1$H (CDCl$_3$, 500 MHz): δ 0.82, (d, J 6.1, 3H), 0.94 (d, J 5.4, 3H), 1.03 (s, 3H), 1.19 (td, J 13.8, 4.1, 1H), 1.16-1.24 (m, 1H), 1.30-1.39 (m, 1H), 1.45 (td, J 13.6, 5.1, 1H), 1.50-1.56 (m, 2H), 1.68 (ddd, J 13.6, 6.7, 1.9, 1H), 1.98 (t, J 14.4, 1H), 2.28 (ddt, J 15.7, 4.6, 2.3, 1H), 2.44 (dd, J 14.7, 6.7, 1H), 2.50 (ddd, J 15.0, 4.1, 2.1, 1H) ppm.

$^{13}$C (CDCl$_3$, 125 MHz): δ 16.0 (q), 16.1 (q), 20.5 (q), 30.7 (t), 33.3 (s), 37.7 (t), 38.8 (d), 39.0 (d), 40.4 (t), 40.9 (t), 41.8 (t), 50.2 (d), 212.4 (s) ppm.

(4aSR,8SR,8aSR)-4a,7,8-trimethyloctahydronaphthalen-2(1H)-one $^1$H (CDCl$_3$, 500 MHz): δ 0.78 (d, J 7.4, 3H), 0.89 (d, J 6.9, 3H), 1.42 (s, 3H), 1.28-1.47 (m, 4H), 1.60-1.70 (m, 2H), 1.78-1.86 (m, 2H), 1.98-2.06 (m, 1H), 2.22 (dd, J 15.9, 4.3, 1H), 2.34-2.43 (m, 2H), 2.60 (dd, J 15.9, 6.3 (1H) ppm.

$^{13}$C (CDCl$_3$, 125 MHz): δ 11.9 (q), 18.5 (q), 25.9 (t), 28.6 (q), 32.6 (s), 35.4 (t), 35.5 (d), 36.6 (t), 37.5 (t), 37.9 (d), 42.7 (t), 47.0 (d), 212.8 (s) ppm.

(4aSR,7SR,8SR,8aRS)-4a,7,8-trimethyloctahydronaphthalen-2(1H)-one $^1$H (CDCl$_3$, 500 MHz): δ characteristic signals:—0.78 (d, J 6.7, 3H), 0.83 (d, J 7.0, 3H), 1.05 (s, 3H).

$^{13}$C (CDCl$_3$, 125 MHz): δ 12.1 (q), 15.7 (q), 17.2 (q), 28.6 (t), 33.7 (s), 33.9 (d), 34.4 (d), 34.8 (t), 38.1 (t) 41.0 (t), 41.3 (t), 43.4 (d), 212.5 (s) ppm.

c) Preparation of a mixture of 2-ethynyl-4a,7,8-trimethyldecahydronaphthalen-2-ol and 2-ethynyl-4a,5,8-trimethyldecahydronaphthalen-2-ol A solution of the cis and trans decalone obtained in the previous step (26.7 g, 137 mmol) in THF (11 mL) was added slowly dropwise to a stirred solution of ethynyl magnesium bromide (0.5 M in THF, 385 mL, 192 mmol) cooled to 4° C. in an ice bath. The solution was allowed to warm to ambient temperature and stirred overnight. The reaction mixture was poured into ice and extracted with diethyl ether, the organic phase washed with saturated NH$_4$Cl solution, then brine, dried over Na$_2$SO$_4$, filtered and the solvents removed in vacuo to yield the crude propargylic alcohol as a complex mixture of isomers, 26.0 g as a brown oil. The complex mixture of isomeric alcohols was used without further purification in the next step.

d) Preparation of a mixture of 1-(4a,7,8-trimethyl-3,4,4a,5,6,7,8,8a-octahydronaphthalen-2-yl)ethan-1-one, 1-(4a,7,8-trimethyl-1,4,4a,5,6,7,8,8a-octahydronaphthalen-2-yl)ethan-1-one, 1-(4a,5,8-trimethyl-3,4,4a,5,6,7,8,8a-octahydronaphthalen-2-yl)ethan-1-one and 1-(4a,5,8-trimethyl-1,4,4a,5,6,7,8,8a-octahydronaphthalen-2-yl)ethan-1-one The mixture of propargylic alcohols (19.0 g, 86 mmol) was dissolved in formic acid (55 mL, 90%) and heated at 80° C. for 2 hours then cooled and poured into a mixture of ice and water. The aqueous phase was extracted with pentane, the organic phase washed with water, then saturated NaHCO$_3$ solution, brine, dried over Na$_2$SO$_4$, filtered and the solvents removed in vacuo to yield the crude enone as a complex mixture of isomers, 20.0 g. Further purification by vacuum distillation with a Vigreux column, 0.2 mbar, b.p. 65-90° C., gave the enone as a mixture of isomers comprising 1-((4aRS,8aRS)-4a,7,8-trimethyl-1,2,3,4,4a,5,6,8a-octahydronaphthalen-2-yl)ethan-1-one, 1-(4a,7,8-trimethyl-3,4,4a,5,6,7,8,8a-octahydronaphthalen-2-yl)ethan-1-one, 1-(4a,7,8-trimethyl-1,4,4a,5,6,7,8,8a-octahydronaphthalen-2-yl)ethan-1-one, 1-(4a,5,8-trimethyl-3,4,4a,5,6,7,8,8a-octahydronaphthalen-2-yl)ethan-1-one and 1-(4a,5,8-trimethyl-1,4,4a,5,6,7,8,8a-octahydronaphthalen-2-yl)ethan-1-one, 9.8 g, 50% yield.

Small quantities of some individual isomers were isolated to yield 1-((4aRS,8aRS)-4a,7,8-trimethyl-1,2,3,4,4a,5,6,8a-octahydronaphthalen-2-yl)ethan-1-one $^1$H (CDCl$_3$, 500 MHz): δ 0.85 (s, 3H), 0.90-1.05 (m, 4H), 1.12 (q, J 12.8, 1H), 1.34 (td, J 12.6, 3.9, 1H), 1.41-1.54 (m, 1H), 1.55 (s, 3H), 1.62 (s, 3H), 1.58-1.70 (m, 4H), 1.94-2.07 (m, 4H), 2.13 (s, 3H), 2.30 (tt, J 12.2, 3.4, 1H) ppm.

$^{13}$C (CDCl$_3$, 125 MHz): δ 18.5 (q), 18.8 (q), 24.0 (t), 26.8 (q), 26.9 (t), 27.9 (q), 29.4 (t), 31.2 (t), 31.6 (s), 39.8 (t), 48.4, 52.1 (d), 124.1, 127.7 (s), 212.2 (s) ppm.

1-((4aSR,8SR,8aRS)-4a,7,8-trimethyl-3,4,4a,5,6,7,8,8a-octahydronaphthalen-2-yl)ethan-1-one $^1$H (CDCl$_3$, 500 MHz): δ 0.87 (d, J 6.4, 3H), 0.85-0.89 (m, 2H), 1.03 (s, 3H), 1.06 (d, J 7.0, 3H), 1.22 (td, J 12.8, 3.9, 1H), 1.35-1.47 (m, 4H), 1.51 (ddd, J 12.9, 6.3, 1.3, 1H), 1.63-1.73 (m, 2H), 1.96-2.00 (m, 1H), 2.09-2.18 (m, 1H), 2.29 (s, 3H), 6.85 (bs, 1H) ppm.

$^{13}$C (CDCl$_3$, 125 MHz): δ 19.8 (q), 20.2 (q), 20.3 (t), 25.4 (q), 26.4 (q), 30.0 (t), 31.3 (t), 32.1 (s), 34.8 (d), 36.3 (d), 36.4 (t), 48.9 (d), 139.2 (s), 140.8 (d), 199.4 (s) ppm.

Example 2

Synthesis of Compounds of Formula (I)—Preparation of a Mixture of 1-((4aSR,8SR,8aSR)-4a,7,8-trimethyl-3,4,4a,5,6,7,8,8a-octahydronaphthalen-2-yl)ethan-1-one and 1-((4aSR,8SR,8aRS)-4a,7,8-trimethyl-1,4,4a,5,6,7,8,8a-octahydronaphthalen-2-yl)ethan-1-one a) Preparation of (4aRS,8RS,8aRS)-2-ethynyl-4a,7,8-trimethyldecahydronaphthalen-2-ol A solution of ethynyl magnesium chloride (10.7 mL, 0.5 M, 5.35 mmol) was added to a solution of (4aSR,8SR,8aRS)-4a,7,8-trimethyloctahydronaphthalen-2(1H)-one (isolated from example 1 step b), 800 mg, 4.12 mol) in THF (2 mL) cooled to 0° C. After warming to ambient temperature and stirring for a further 2 hrs the reaction was poured into a mixture of ice and saturated NH$_4$Cl, and extracted with ether. The organic phase was washed with brine and dried over Na$_2$SO$_4$, filtered and the solvents removed in vacuo to yield the crude alcohol, 800 mg, which was used without further purification in the next step.

$^1$H (CDCl$_3$, 500 MHz): δ 0.83 (s, 3H), 0.85 (d, J 6.1, 3H), 0.92 (d, J 6.4, 3H), 0.94-1.07 (m, 5H), 1.13 (ddd, J 13.0, 10.2, 2.7, 1H), 1.19 (dd, J 12.8, 4.2, 1H), 1.24-1.52 (m, 5H), 1.75 (td, J 12.7, 4.7, 1H), 1.80-1.87 (m, 1H), 2.02 (dt, J 12.3, 2.5, 1H), 2.21 (bs, 1H), 2.47 (s, 1H) ppm.

13C:111630

$^{13}$C (CDCl$_3$, 125 MHz): δ 16.4 (q), 16.6 (q), 20.8 (q), 30.8 (t), 33.2 (s), 35.3 (t), 37.5 8d), 38.6 (t), 39.2 (t), 40.9 (t), 47.9 (d), 70.6 (s), 72.1 (s), 87.8 (s) ppm.

b) Preparation of a mixture of 1-((4aSR,8SR,8aSR)-4a,7,8-trimethyl-3,4,4a,5,6,7,8,8a-octahydronaphthalen-2-yl)ethan-1-one and 1-((4aSR,8SR,8aRS)-4a,7,8-trimethyl-1,4,4a,5,6,7,8,8a-octahydronaphthalen-2-yl)ethan-1-one Conditions reported in example 1 d) were applied to (4aRS,8RS,8aRS)-2-ethynyl-4a,7,8-trimethyldecahydronaphthalen-2-ol providing a mixture of 1-((4aSR,8SR,8aSR)-4a,7,8-trimethyl-3,4,4a,5,6,7,8,8a-octahydronaphthalen-2-yl)ethan-1-one and 1-((4aSR,8SR,8aRS)-4a,7,8-trimethyl-1,4,4a,5,6,7,8,8a-octahydronaphthalen-2-yl)ethan-1-one.

Major isomer: 1-((4aSR,8SR,8aRS)-4a,7,8-trimethyl-1,4,4a,5,6,7,8,8a-octahydronaphthalen-2-yl)ethan-1-one.

$^1$H (CDCl$_3$, 500 MHz): δ 0.75 (s, 3H), 0.93 (d, J 6.2, 3H), 0.78-0.93 (m, 4H), 1.07-1.62 (m, H), 2.01 (bm, 1H), 2.29 (s, 3H), 2.61 (dd, J 18, 3.5, 1H), 6.81 (bm, 1H) ppm.

$^{13}$C (CDCl$_3$, 125 MHz): δ 16.3 (q), 17.5 (q), 20.7 (q), 25.3 (t), 30.8 (t), 39.1 (d), 39.4 (d), 40.8 (t), 43.5 (t), 45.6 (d), 139.2 (s), 141.7 (d), 199.4 (s) ppm.

Example 3

Synthesis of Compounds of Formula (I)—Preparation of a Mixture of 1-((4aSR,7RS)-4a,7,8-trimethyl-3,4,4a,5,6,7-hexahydronaphthalen-2-yl)ethan-1-one a) Preparation of (4aSR,8SR)-4a,7,8-trimethyl-4,4a,5,6,7,8-hexahydronaphthalen-2(3H)-one A solution of the enone mixture obtained in a previous step (20.0 g, 104 mmol) in THF (25 mL) was added slowly dropwise to a stirred solution of ethynyl magnesium bromide (0.5 M in THF, 354 mL, 177 mmol) cooled to 4° C. in an ice bath. The solution was allowed to warm to ambient temperature and stirred overnight. The reaction mixture was poured into a mixture of ice/saturated NH$_4$Cl solution and extracted with diethyl ether, the organic phase washed with saturated NH$_4$Cl solution, then brine, dried over Na$_2$SO$_4$, filtered and the solvents removed in vacuo to yield the crude propargylic alcohol as a complex mixture of isomers, 20.0 g as a brown oil. The complex mixture of isomeric alcohols was used without further purification in the next step.

b) Preparation of 1-((4aSR,7RS)-4a,7,8-trimethyl-3,4,4a,5,6,7-hexahydronaphthalen-2-yl)ethan-1-one A solution of the propargylic alcohol mixture (20.0 g, 92 mmol) in ethyl acetate (50 mL) was treated with Amberlyst A-15 (10.0 g) and the suspension heated under reflux for 4 hours then cooled and filtered through a small plug of silica (3 cm) and washed with ethyl acetate. The combined organic phase was washed with saturated sodium bicarbonate solution, then brine, dried over Na$_2$SO$_4$, filtered and the solvents removed in vacuo to yield the crude dienone as a mixture of isomers 87:13. Further purification by Fischer distillation 0.15 mbar b.p 70-85° C. gave the pure dienone as a mixture of isomers (87:13), 12.8 g, 64%.

Major isomer: 1-((4aSR,7RS)-4a,7,8-trimethyl-3,4,4a,5,6,7-hexahydronaphthalen-2-yl)ethan-1-one $^1$H (CDCl$_3$, 500 MHz): δ 0.91 (s, 3H), 1.00 (d, J 7.0, 3H), 1.08 (d, J 7.2, 3H), 1.27 (tt, J 12.3, 5.4, 1H), 1.31-1.57 (m, 3H), 1.60 (ddd, J 13, 5.9, 1.3, 1H), 1.88 (s, 3H), 2.15-2.30 (m, 2H), 2.35 (d, J 1.6, 3H), 2.49 (dt, J 19, 4.6, 1H), 7.43 (d, J 1.6, 1H) ppm.

Example 4

Preparation of a Perfuming Composition

A perfuming composition, of the woody type, was prepared by admixing the following ingredients:

| Parts by weight | Ingredient |
|---|---|
| 200 | Ambrox ®[1] |
| 400 | Bergamot oil |
| 40 | 10%* 7-Methy1-2H,4H-1,5-benzodioxepin-3-one |
| 20 | Cardamon oil |
| 600 | Lemon oil |
| 100 | Coumarin |
| 20 | Alpha damascone |
| 200 | (1'R,E)-2-ethyl-4-(2',2',3'-trimethyl-3'-cyclopenten-1'-yl)-2-buten-1-ol |
| 1000 | Dihydromyrcenol |
| 200 | (1-Ethoxyethoxy)cyclododecane |
| 200 | Hedione ®[2] HC |
| 200 | 3-(1,3-Benzodioxol-5-yl)-2-methylpropanal |
| 200 | Helvetolide ®[3] |
| 200 | Iralia ®[4] Total |
| 20 | Nutmeg oil |
| 2000 | Hedione ®[5] |
| 10 | Neobutenone ®[6] Alpha |
| 20 | Pink pepper oil |
| 100 | Nirvanol ®[7] |
| 100 | (Z)-3-Hexen-1-ol salicylate |
| 10 | 2-Ethyl-4,4-dimethylcyclohexanone |
| 60 | Vetiver oil |
| 100 | (+)-8,13:13,20-Diepoxy-15,16-dinorlabdane |
| 6000 | |

[1] (−)-(8R)-8,12-epoxy-13,14,15,16-tetranorlabdane[a]
[2] high cis methyl dihydrojasmonate[a]
[3] (1S,1'R)-2-[1-(3',3'-dimethyl-1'-cyclohexyl)ethoxy]-2-methylpropyl propanoate[a]
[4] mixture of methylionones isomers[a]
[5] methyl dihydrojasmonate[a]
[6] 1-(5,5-dimethyl-1-cyclohexen-1-yl)-4-penten-1-one[a]
[7] 3,3-dimethyl-5-(2,2,3-trimethyl-3-cyclopenten-1-yl)-4-penten-2-ol[a]
*in dipropyleneglycol
[a] origin: Firmenich SA, Geneva, Switzerland The addition of 4000 parts by weight of compound as obtained in Example 1 to the above-described composition imparted to the latter a reinforced rooty/powdery, ambery and smoky characters by blending very well with woody-vetiver (Vetiver oil), amber (Ambrox©) and powdery-violet (Iralia® Total) elements present in the original formula. Moreover, this ingredient twists this formula in a more masculine direction. Said compound is the most powerful in bottom and top note.

When instead of compound as obtained in Example 1 was added the same amount of a mixture of 1-((4aRS,8RS,8aSR)-4a,8-dimethyl-3,4,4a,5,6,7,8,8a-octahydronaphthalen-2-yl)ethan-1-one, 1-((4aRS,8RS,8aRS)-4a,8-dimethyl-3,4,4a,5,6,7,8,8a-octahydronaphthalen-2-yl)ethan-1-one, 1-((4aRS,8RS,8aSR)-4a,8-dimethyl-1,4,4a,5,6,7,8,8a-octahydronaphthalen-2-yl)ethan-1-one and 1-((4aRS,8RS,8aRS)-4a,8-dimethyl-1,4,4a,5,6,7,8,8a-octahydronaphthalen-2-yl)ethan-1-one (20:12:39:28), then said ingredient provided a similar effect to the one of Example 1 with the lighter powdery character. This ingredient is less powerful and more unisex so more versatile.

When instead of compound as obtained in Example 1 was added the same amount of prior art's 1-[(4aRS,8SR,8aSR)-4a,8-dimethyl-3,4,4a,5,6,7,8,8a-octahydro-2-naphthalenyl]ethanone, then this ingredient pushed the fruity-Dasmascone (Damascone Alpha) element (an element not observed with the invention's compounds) and twists the woody accord in a more cedar like direction. This ingredient is the less powerful.

The invention claimed is:

1. A method to confer, enhance, improve or modify odor properties of a perfuming composition or of a perfumed article, the method comprising adding to said composition or article an effective amount of at least a compound of formula

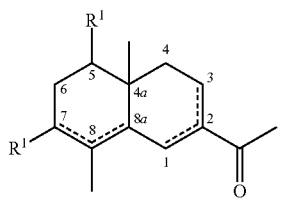

(I)

in a form of any one of its stereoisomers or a mixture thereof, wherein dotted lines represent a carbon-carbon single bond or a carbon-carbon a double bond; and one R¹ group represents a hydrogen atom and a second R¹ group represents a methyl group.

2. The method according to claim 1, characterized in that the two methyl groups at carbon 4a and 8 are in an anti-configuration.

3. The method according to claim 1, characterized in that the compound of formula (I) is a compound of formula

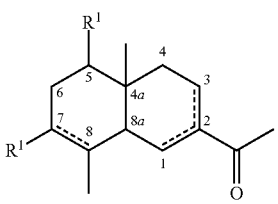

(II)

in a form of any one of its stereoisomers or a mixture thereof, and wherein at least one dotted line represents a carbon-carbon single bond and the others a carbon-carbon double bond; and one R¹ group represents a hydrogen atom and a second R¹ group represents a methyl group.

4. The method according to claim 3, characterized in that the compound of formula (I) is a compound of formula

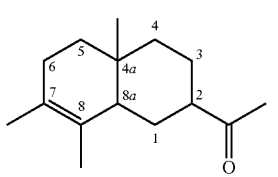

(III)

in a form of any one of its stereoisomers or a mixture thereof.

5. The method according to claim 1, characterized in that the compound of formula (I) is a compound of formula

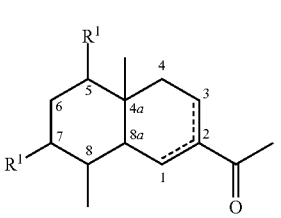

(IV)

in a form of any one of its stereoisomers or a mixture thereof, and wherein one dotted line represents a carbon-carbon single bond and the other a carbon-carbon double bond; and one R¹ group represents a hydrogen atom and a second R¹ group represents a methyl group.

6. The method according to claim 5, characterized in that the compound of formula (I) is a compound of formula

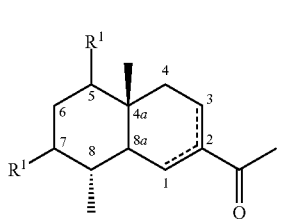

(V)

in a form of any one of its stereoisomers or a mixture thereof, wherein bold and hatched lines indicate a relative or absolute configuration; dotted lines represent a carbon-carbon single bond or a carbon-carbon double bond; and one R¹ group represents a hydrogen atom and a second R¹ group represents a methyl group.

7. The method according to claim 5, characterized in that the compound of formula (I) is a compound of formula

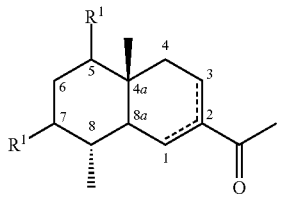

(VI)

in a form of any one of its stereoisomers or a mixture thereof, wherein bold and hatched lines indicate a relative or absolute configuration; and dotted lines represent a carbon-carbon single bond or a carbon-carbon double bond.

8. The method according to claim 5, characterized in that the compound of formula (I) is a compound of formula (VII)

in a form of any one of its stereoisomers or a mixture thereof, wherein bold and hatched lines indicate a relative or absolute configuration; and dotted lines represent a carbon-carbon single bond or a carbon-carbon double bond.

9. The method according to claim 1, characterized in that the compound of formula (I) is 1-((4aRS,8aRS)-4a,7,8-trimethyl-1,2,3,4,4a,5,6,8a-octahydronaphthalen-2-yl) ethan-1-one, 1-((4aRS,7SR,8RS,8aRS)-4a,7,8-trimethyl-1,4,4a,5,6,7,8,8a-octahydronaphthalen-2-yl)ethan-1-one, 1-((4aRS,7RS,8RS,8aRS)-4a,7,8-trimethyl-1,4,4a,5,6,7,8,8a-octahydronaphthalen-2-yl)ethan-1-one, 1-((4aRS,7RS,8RS,8aSR)-4a,7,8-trimethyl-1,4,4a,5,6,7,8,8a-octahydronaphthalen-2-yl) ethan-1-one, 1-((4aRS,7SR,8RS,8aSR)-4a,7,8-trimethyl-1,4,4a,5,6,7,8,8a- octahydronaphthalen-2-yl)ethan-1-one, 1-((4aRS,7SR,8RS,8aSR)-4a,7,8-trimethyl-3,4,4a,5,6,7,8,8a-octahydronaphthalen-2-yl)ethan-1-one, 1-((4aRS,7RS,8RS,8aSR)-4a,7,8-trimethyl-3,4,4a,5,6,7,8,8a-octahydronaphthalen-2-yl)ethan-1-one, 1-((4aRS,7RS,8RS,8aRS)-4a,7,8-trimethyl-3,4,4a,5,6,7,8,8a-octahydronaphthalen-2-yl)ethan-1-one, 1-((4aRS,7SR,8RS,8aRS)-4a,7,8-trimethyl-3,4,4a,5,6,7,8,8a-octahydronaphthalen-2-yl)ethan-1-one 1-((4aSR,5RS,8RS,8aRS)-4a,5,8-trimethyl-1,4,4a,5,6,7,8,8a-octahydronaphthalen-2-yl) ethan-1-one, 1-((4aSR,5SR,8RS,8aRS)-4a,5,8-trimethyl-1,4,4a,5,6,7,8,8a-octahydronaphthalen-2-yl)ethan-1-one, 1-((4aSR,5SR,8RS,8aSR)-4a,5,8-trimethyl-1,4,4a,5,6,7,8,8a-octahydronaphthalen-2-yl)ethan-1-one, 1-((4aSR,5RS,8RS,8aSR)-4a,5,8-trimethyl-1,4,4a,5,6,7,8,8a-octahydronaphthalen-2-yl)ethan-1-one, 1-((4aSR,5RS,8RS,8aSR)-4a,5,8-trimethyl-3,4,4a,5,6,7,8,8a-octahydronaphthalen-2-yl)ethan-1-one, 1-((4aSR,5SR,8RS,8aSR)-4a,5,8-trimethyl-3,4,4a,5,6,7,8,8a-octahydronaphthalen-2-yl)ethan-1-one, 1-((4aSR,5SR,8RS,8aRS)-4a,5,8-trimethyl-3,4,4a,5,6,7,8,8a-octahydronaphthalen-2-yl) ethan-1-one, 1-((4aSR,5RS,8RS,8aRS)-4a,5,8-trimethyl-3,4,4a,5,6,7,8,8a-octahydronaphthalen-2-yl) ethan-1-one and/or mixtures thereof.

10. A compound of formula (I) as defined in claim 1.

11. A perfuming composition comprising
i) at least one compound of formula (I), as defined in claim 10;
ii) at least one ingredient selected from the group consisting of a perfumery carrier and a perfumery base; and
iii) optionally at least one perfumery adjuvant.

12. A perfumed consumer product comprising at least one compound of formula (I), as defined in claim 10.

13. The perfumed consumer product according to claim 12, characterized in that the perfumed consumer product is a perfume, a fabric care product, a body-care product, a cosmetic preparation, a skin-care product, an air care product or a home care product.

14. The perfumed consumer product according to claim 13, characterized in that the perfumed consumer product is a fine perfume, a splash or eau de perfume, a cologne, an shave or after-shave lotion, a liquid or solid detergent, a fabric softener, a fabric refresher, an ironing water, a paper, a bleach, a carpet cleaners, curtain—care products a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, or a foot/hand care products, a hygiene product, an air freshener, a "ready to use" powdered air freshener, a mold remover, furnisher care, wipe, a dish detergent or hard-surface detergent, a leather care product, or a car care product.

\* \* \* \* \*